United States Patent [19]

Simon et al.

[11] Patent Number: 5,059,412

[45] Date of Patent: * Oct. 22, 1991

[54] MACROCYCLIC AMINOPHOSPHONIC ACID COMPLEXES FOR THE TREATMENT OF CALCIFIC TUMORS

[75] Inventors: Jaime Simon, Angleton; David A. Wilson, Richwood; Joseph R. Garlich, Lake Jackson, all of Tex.; David E. Troutner, Columbia, Mo.

[73] Assignee: The Dow Chemical Company, Midland, Mich.

[*] Notice: The portion of the term of this patent subsequent to Nov. 21, 2006 has been disclaimed.

[21] Appl. No.: 284,876

[22] Filed: Dec. 19, 1988

Related U.S. Application Data

[63] Continuation-in-part of Ser. No. 50,263, May 14, 1987, Pat. No. 4,898,724, which is a continuation-in-part of Ser. No. 803,376, Dec. 4, 1985, abandoned, which is a continuation-in-part of Ser. No. 738,010, May 28, 1985, abandoned, which is a continuation-in-part of Ser. No. 616,985, Jun. 4, 1984, abandoned.

[51] Int. Cl.$^5$ .......................... A61K 43/00; C07F 5/00
[52] U.S. Cl. ........................................ 424/1.1; 534/10; 424/9; 424/DIG. 6
[58] Field of Search ...................... 424/1.1, 9; 534/10, 534/14, 15

[56] References Cited

U.S. PATENT DOCUMENTS

| | | |
|---|---|---|
| 3,965,254 | 6/1976 | Tofe et al. ............... 424/1.1 |
| 4,017,595 | 4/1977 | Subramanian et al. ........ 424/1.1 |
| 4,187,284 | 2/1980 | Rolleston et al. ............ 424/1.1 |
| 4,853,209 | 8/1989 | Kaplan et al. .............. 424/1.1 |
| 4,882,142 | 11/1989 | Simon et al. ............... 424/1.1 |
| 4,885,363 | 12/1989 | Tweedle et al. ............. 424/9 X |
| 4,898,724 | 2/1990 | Simon et al. ............... 424/1.1 |
| 4,957,939 | 9/1990 | Gries et al. ............... 424/9 X |
| 4,976,950 | 12/1990 | Simon et al. ............... 424/1.1 |

FOREIGN PATENT DOCUMENTS 164843 12/1985 European Pat. Off. ............ 424/1.1

OTHER PUBLICATIONS

Inorg. Chem. 28(17), 3336–3341 (1989); Three cyclic Aminomethylenephosphonic acids.

Inorganica Chim. Acta 139, 137–139, (1987); DOTMP complexed.

J. Magn. Reson. 76, 528–533 (Feb. 1988); First use of the Dy–DOTMP complex.

Izv. Akad. Nauk. SSSR, Ser. Khim. 4, 835–843 (Apr. 1964), Trans. in Bull. Acad. Sci. USSR, Div. of the Chem. Sci 33(4), 769 (Apr. 1984); cyclic amino phosphonic acids.

Izv. Akad. Nauk. SSSR, Ser. Khim. 4, 844–849 (Apr. 1984), Trans. in Bull. Acad. Sci. USSR, Div. of the Chem. Sci. 33(4), 777 (Apr. 1984); Synthesis of DOTMP from the cyclic amine.

Teor. Eksp. Khim. 21(6), 660–669 (Nov.–Dec. 1985); A theoretical conformational analysis of DOTMP and a triazacyclic phosphonic acid.

Teor. Eksp. Khim. 22(6), 655–661 (Nov.–Dec. 1986); Theoretical molecular mechanics calculations of complex forming conformations of DOTMP.

Izv. Akad. Nauk. SSSR, Ser. Khim. 2, 413–417 (Apr. 1987); discloses the preparation of DOTMP as an intermediate in the preparation of the cyclo–dependent compounds.

Chemical Abstracts 87:179938h (1977), G. Subramanian et al.

Int. J. App. Rad. and Isotopes, vol. 14 (1963), Rosoff et al., pp. 129–135.

Primary Examiner—Richard D. Lovering
Assistant Examiner—John M. Covert
Attorney, Agent, or Firm—Karen L. Kimble

[57] ABSTRACT

Particle emitting radionuclides, e.g. Samarium-153, have been complexed with certain macrocyclic aminophosphonic acids wherein the nitrogen and phosphorus are interconnected by an alkylene group or substituted alkylene group. These complexes have been found useful in compositions and formulations for the therapeutic treatment of calcific tumors in animals.

88 Claims, No Drawings

MACROCYCLIC AMINOPHOSPHONIC ACID COMPLEXES FOR THE TREATMENT OF CALCIFIC TUMORS

CROSS-REFERENCE TO RELATED APPLICATION

This application is a continuation-in-part of our co-pending application Ser. No. 050,263 filed May 14, 1987, now U.S. Pat. No. 4,898,724, issued Feb. 6, 1990 which is a continuation-in-part of Ser. No. 803,376 filed Dec. 4, 1985, now abandoned, which is a continuation-in-part of Ser. No. 738,010 filed May 28, 1985, now abandoned, which is a continuation-in-part of Ser. No. 616,985, filed June 4, 1984, now abandoned.

BACKGROUND OF THE INVENTION

The present invention relates to macrocyclic aminophosphonic acid complexes for the treatment of cancer, especially the treatment of calcific tumors, to the method of treatment of calcific tumors, and to compositions having as their active ingredient a radionuclide complexed with a macrocyclic aminophosphonic acid.

The development of bone metastases is a common and often catastrophic event for a cancer patient. The pain, pathological fractures, frequent neurological deficits and forced immobility caused by these metastatic lesions significantly decrease the quality of life for the cancer patient. The number of patients that contract metastatic disease is large since nearly 50% of all patients who contract breast, lung or prostate carcinoma will eventually develop bone metastases. Bone metastases are also seen in patients with carcinoma of the kidney, thyroid, bladder, cervix and other tumors, but collectively, these represent less than 20% of patients who develop bone metastases. Metastatic bone cancer is rarely life threatening and occasionally patients live for years following the discovery of the bone lesions. Initially, treatment goals center on relieving pain, thus reducing requirements for narcotic medication and increasing ambulation. Clearly, it is hoped that some of the cancers can be cured.

The use of radionuclides for treatment of cancer metastatic to the bone dates back to the early 1950's. It has been proposed to inject a radioactive particle-emitting nuclide in a suitable form for the treatment of calcific lesions. It is desirable that such nuclides be concentrated in the area of the bone lesion with minimal amounts reaching the soft tissue and normal bone. Radioactive phosphorus (P-32 and P-33) compounds have been proposed, but the nuclear and biolocalization properties limit the use of these compounds. (Kaplan, E., et al., *Journal of Nuclear Medicine*, 1(1), p. 1, 1960); (U.S. Pat. No. 3,965,254).

Another attempt to treat bone cancer has been made using phosphorus compounds containing a boron residue. The compounds were injected into the body (intravenously) and accumulated in the skeletal system. The treatment area was then irradiated with neutrons in order to activate the boron and give a therapeutic radiation dose. (U.S. Pat. No. 4,399,817).

The use of radionuclides for calific tumor therapy is discussed in published European patent application 176,288 where the use of Sm-153, Gd-159, Ho-166, Lu-177 or Yb-175 complexed with certain ligands selected from ethylenediaminetetraacetic acid (EDTA) or hydroxyethylenediaminetriacetic acid (HEEDTA) is disclosed.

In the above mentioned procedures, it is not possible to give therapeutic doses to the tumor without substantial damage to normal tissues. In many cases, especially for metastatic bone lesions, the tumor has spread throughout the skeletal system and amputation or external beam irradiation is not practical. (*Seminars in Nuclear Medicine*, Vol. IX, No. 2, April, 1979).

The use of Re-186 complexed with a diphosphonate has also been proposed. [Mathieu, L. et al., *Int. J. Applied Rad. & Isotopes*, 30, 725–727 (1979); Weinenger, J., Ketring, A. R., et al., *Journal of Nuclear medicine*, 24(5), P125 (1983)]. However, the preparation and purification needed for this complex limits its utility and wide application.

Strontium-89 has also been proposed for patients with metastatic bone lesions. However, the long half-life (50.4 days), high blood levels and low lesion to normal bone ratios limit the utility. [Firusian, N., Mellin, P., Schmidt, C. G., *The Journal of Urology*, 116, 764 (1976): Schmidt, C. G., Firusian, N., *Int. J. Clin. Pharmacol.*, 93, 199–205, (1974)].

A palliative treatment of bone metastases has been reported which employed I-131 labelled α-amino(3-iodo-4-hydroxybenzylidene)diphosphonate [Eisenhut, M., *Journal of Nuclear Medicine*, 25(12), 1356–1361 (1984)]. The use of radioiodine as a therapeutic radionuclide is less than desirable due to the well known tendency of iodine to localize in the thyroid. Eisenhut lists iodide as one of the possible metabolites of this compound.

The present invention is directed to at least one composition comprised of a radionuclide complexed with a macrocyclic aminophosphonic acid containing 1,4,7,10-tetraazacyclododecane, or its physiologically acceptable salt, which causes minimal damage to normal tissue when administered in the method of the invention. Surprisingly, the present complex is more effective at a lower ligand to metal molar ratio than has been known previously in the art.

SUMMARY OF THE INVENTION

This invention concerns certain particleemitting radionuclides which have been complexed with certain macrocyclic aminophosphonic acids, i.e. macrocyclic aminophosphonic acids containing 1,4,7,10-tetraazacyclododecane as the macrocyclic moiety and wherein the nitrogen and phosphorus atoms are interconnected by an alkylene or substituted alkylene group, and physiologically acceptable salts thereof. The preferred macrocyclic aminophosphonic acid is 1,4,7,10-tetraazacyclododecanetetramethylenephosphonic acid (DOTMP). The composition can be administered as a formulation with suitable pharmaceutically acceptable carriers. The present includes the use of the complex or composition in combination with other drugs and/or radiation sources.

Certain compositions containing these complexes have been found useful for therapy of calcific tumors in animals. The administration of the therapeutic compositions can be palliative to the animal, for example by alleviating pain and/or inhibiting tumor growth and/or causing regression of tumors and/or destroying the tumors.

In addition the present invention also includes formulations having at least one of the radionuclide(s) complexed with at least one of the macrocyclic aminophosphonic acids of the invention and a pharmaceutically acceptable carrier, excipient or vehicle therefor. The methods for preparing such formulations are well known. The formulations are sterile and may be in the form of a suspension, injectable solution or other suitable pharmaceutically acceptable formulations. Pharmaceutically acceptable suspending media, with or without adjuvants, may be used.

The present invention contemplates the use of one or more other agents or treatments which assist in therapy of calcific tumors when used in conjunction with the compositions or formulations described herein.

DETAILED DESCRIPTION OF THE INVENTION

The invention is directed to compositions having at least one of the radionuclide(s) complexed with at least one of the macrocyclic aminophosphonic acids of the invention and physiologically acceptable salts thereof. Also the invention includes formulations having at least one of the radionuclide(s) complexed with at least one of the macrocyclic aminophosphonic acids of the invention and physiologically acceptable salts thereof and a pharmaceutically acceptable carrier, excipient or vehicle therefor.

The compositions and formulations of this invention are used for the therapeutic treatment of calcific tumors in animals. These compositions contain certain radionuclides complexed with certain macrocyclic aminophosphonic acids, or physiologically acceptable salts thereof. As will be more fully discussed later, the properties of the radionuclide, of the macrocyclic aminophosphonic acid and of the complex formed therefrom are important considerations in determining the effectiveness of any particular composition employed for such treatment.

Particle-emitting radionuclides employed in the compositions of the invention are capable of delivering a high enough localized ionization density to alleviate pain and/or inhibit tumor growth and/or cause regression of tumors, and/or destroy the tumor and are capable of forming complexes with the macrocyclic aminophosphonic acid ligands described herein. The radionuclides found to be useful in the practice of the invention are Samarium-153 (Sm-153), Holmium-166 (Ho-166), Ytterbium-175 (Yb-175), Lutetium-177 (Lu-177), and Gadolinium-159 (Gd-159).

The macrocyclic aminophosphonic acids which have been found useful in the compositions of this invention are macrocyclic aminophosphonic acids containing 1,4,7,10-tetraazacyclododecane as the macrocyclic moiety and wherein the amine nitrogen and the phosphorus of the phosphonic acid moiety are interconnected by an alkylene or substituted alkylene radical having the formula

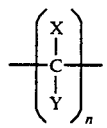

wherein X and Y are independently selected from the group consisiting of hydrogen, hydroxyl, carboxyl, phosphonic, and hydrocarbon radicals having from 1-8 carbon atoms and physiologioally acceptable salts of the acid radicals and n is 1-3 with the proviso that when n>1 each X and Y may be the same as or different from the X and Y of any other carbon atom.

The following structural formula represents some of the ligands which can be used in the compositions of this invention:

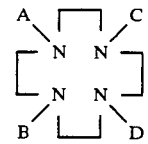

wherein substituents A, B, C, and D are independently selected from hydrogen, hydrocarbon radicals having from 1-8 carbon atoms,

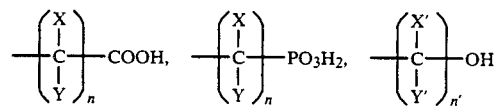

and physiologically acceptable salts of the acid radicals wherein X, Y, and n are as previously defined, X' and Y' are independently hydrogen, methyl or ethyl radicals, n' is 2 or 3, with the proviso that at least two of said nitrogen substituents are a phosphonic acid group as previously described herein.

The radionuclide complexed with the macrocyclic aminophosphonic acid is at least one radionuclide selected from the group consisting of Sm-153, Gd-159, Ho-166, Lu-177, and Yb-175.

For the purpose of convenience, the radionuclide-macrocyclic aminophosphonic acid compositions will frequently be referred to as "radionuclide compositions" or "compositions" and the macrocyclic aminophosphonic acid derivative referred to as the "ligand" or "chelant".

As used herein, the term "animals" means warm blooded mammals, including humans, and is meant to encompass animals in need of treatment for calcific tumors.

The term "calcific tumors" includes primary tumors, where the skeletal system is the first site of involvement, invasive tumors where the primary tumor invades the skeletal system or other tissue tumors which calcify, and metastatic bone cancer where the neoplasm spreads from other primary sites, e.g. prostate and breast, into the skeletal system.

For the purpose of the present invention, the complexes described herein and physiologically acceptable salts thereof are considered equivalent in the therapeutically effective compositions. Physiologically acceptable salts refer to the acid addition salts of those bases which will form a salt with at least one acid group of the ligand or ligands employed and which will not cause a significant adverse physiological effect when administered to an animal at dosages consistent with good pharmacological practice; some examples of such practice are described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like. Physiologically acceptable salts may be prepared by treating the macrocyclic aminophosphonic acid with an appropriate base.

The formulations of the present invention are in the solid or liquid form containing the active radionuclide complexed with the ligand. These formulations may be in kit form such that the two components are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the free acid. In solution form the complex (or when desired the separate components) is dissolved in a pharmaceutically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50% of the organic solvent by volume.

Injectable suspensions as compositions of the present invention require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickners such as carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances which effect the hydrophibicity, density, and surface tension of the liquid suspension medium can assist in making injectable suspensions in individual cases. For example, silcone antifoams, sorbitol, and sugars are all useful suspending agents.

Complexes employed in the compositions or formulations of the present invention must fit certain criteria insofar as possible.

While the properties of the radionuclide are important, the overall properties of the composition containing the radionuclide-macrocyclic aminophosphonic acid complex is the determining factor. The disadvantages of any one property may be overcome by the superiority of one or more of the properties of either ligand or radionuclide and their combination, as employed in the composition must be considered in toto.

There is a need for compositions possessing the following criteria by which it is possible to deliver therapeutic radiation doses to calcific tumors with minimal doses to soft tissue.

The radionuclide must be delivered preferentially to the bone rather than to soft tissue. Most particularly, uptake in either liver or blood is undesirable.

The radionuclide should be cleared rapidly from non-osseous tissue to avoid unnecessary damage to such tissues, e.g., it should clear rapidly from the blood.

The proposed use for the compositions and formulations of this invention is the therapeutic treatment of calcific tumors in animals. As used herein, the term "calcific tumors" includes primary tumors where the skeletal system is the first site of involvement, or other tissue tumors which calcify, or metastatic bone cancer where the neoplasm spreads from other primary sites, such as prostate and breast, into the skeletal system. This invention provides a means of alleviating pain and/or reducing the size of, and/or inhibiting the growth and/or spread of, or causing regression of and/or destroying the calcific tumors by delivering a therapeutic radiation dose.

The composition or formulation may be administered as a single dose or as multiple doses over a longer period of time. Delivery of the radionuclide to the tumor must be in sufficient amounts to provide the benefits referred to above.

The "effective amount" or "therapeutically effective amount" of radionuclide composition to be administered to treat calcific tumors will vary according to factors such as the age, weight and health of the patient, the calcific tumor being treated, the treatment regimen selected as well as the nature of the particular radionuclide composition to be administered. For example, less activity will be needed for radionuclides with longer half lives. The energy of the emissions will also be a factor in determining the amount of activity necessary. The compositions of this invention may also be employed at dose which are useful but not therapeutic.

A suitable dose of the composition or formulation of this invention for use in this invention is at least about 0.02 mCi per Kg of body weight. A "therapeutically effective dose" of the composition or formulation of this invention for use in this invention is at least about 0.2 mCi per Kg of body weight.

The effective amount used to treat calcific tumors will typically be administered, generally by administration into the bloodstream, in a single dose. The amounts to be administered to achieve such treatment are readily determined by one skilled in the art employing standard procedures.

The radionuclide and ligand may be combined under any conditions which allow the two to form a complex. Generally, mixing in water at a controlled pH (the choice of pH is dependent upon the choice of ligand and radionuclide) is all that is required. The complex formed is by a chemical bond and results in a relatively stable radionuclide composition, e.g. stable to the disassociation of the radionuclide from the ligand.

The macrocyclic aminophosphonic acid complexes when administered at a ligand to metal molar ratio of at least about 1:1, preferrably about 1:1 to about 3:1, more preferrably about 1:1 to about 1.5:1, give biodistributions that are consistent with excellent skeletal agents. By contrast, certain other aminophosphonic acid complexes result in some localization in soft tissue (e.g. liver) if excess amounts of ligand are not used. A large excess of ligand is undesirable since uncomplexed ligand may be toxic to the patient or may result in cardiac arrest or hypocalcemic convulsions. In addition, the macrocyclic aminophosphonic acid ligands are useful when large amounts of metal are required (i.e. for metals that have a low specific activity). In this case, the macrocyclic aminophosphonic acid ligands have the ability to deposit larger amounts of activity in the bone than is possible when using non-cyclic aminophosphonic acid ligands.

A preferred embodiment of the present invention is a therapeutically effective composition or formulation containing complexes of at least one radionuclide selected from Gd-159, Ho-166, Lu-177, Sm-153 and Yb-175 with DOTMP or a physiologically acceptable salt(s) thereof.

Combinations of the various above noted radionuclides can be administered for the therapeutic treatment of calcific tumors. The combinations can be complexed as herein described by complexing them simultaneously, mixing two separately complexed radionuclides, or administering two different complexed radionuclides sequentially. It may be possible to achieve the same beneficial results of high delivery of the radionuclide to the area of the tumor, but with little soft tissue damage, by administering the ligand and the radionuclide in a manner which allows formation of the radionuclidechelant complex in situ such as by simultaneous or near simultaneous administration of the radionuclide and an appropriate amount of ligand or by the administration of ligand and a radionuclide complexed with a weaker ligand, i.e., one which undergoes ligand exchange with the ligands of this invention, such that the desired radionuclide-chelant complex is formed via ligand exchange in situ. The composition or formulation may be administered as a single dose or as multiple doses over a longer period of time.

Aminophosphonic acids can be prepared by a number of known synthetic techniques. Of particular importance is the reaction of a compound containing at least one reactive amine hydrogen with a carbonyl compound (aldehyde or ketone) and phosphorous acid or derivative thereof. The amine precursor (1,4,7,10-tetraazacyclododecane) employed in making the macrocyclic aminophosphonic acids is a commercially available material.

Methods for carboxyalkylating to give amine derivatives containing a carboxyalkyl group are well known (U.S. Pat. No. 3,726,912) as are the methods which give alkyl phosphonic and hydroxyalkyl (U.S. Pat. No. 3,398,198) substituents on the amine nitrogens.

Radionuclides can be produced in several ways. In a nuclear reactor, a nuclide is bombarded with neutrons to obtain a radionuclide, e.g.

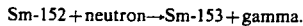

Sm-152+neutron→Sm-153+gamma.

Another method of obtaining radionuclides is by bombarding nuclides with linear accelerator or cyclotron-produced particles. Yet another way of obtaining radionuclides is to isolate them from fission product mixtures. The method of obtaining the radionuclide is not critical to the present invention.

To irradiate $Sm_2O_3$ for production of Sm-153, the desired amount of target was first weighed into a quartz vial, the vial was flame sealed under vacuum and welded into an aluminum can. The can was irradiated for the desired length of time, cooled for several hours and opened remotely in a hot cell. The quartz vial was removed and transferred to a glove box, crushed into a glass vial which was then sealed with a rubber septum and an aluminum crimp cap. One milliliter of 1-4 M HCl was then added to the vial via syringe to dissolve the $Sm_2O_3$. Once dissolved, the solution was diluted to the appropriate volume by addition of water. The solution was removed from the original dissolution vial which contains chards of the crushed quartz vial and transferred via syringe to a clean glass serum vial. This solution was then used for complex preparation. Similar procedures were used to prepare Lu-177, Yb-175, Gd-159, and Ho-166.

The invention described herein provides a means of delivering a therapeutic amount of radioactivity to calcific tumors. However, it may also be desirable to administer a "sub-therapeutic" amount (i.e. "useful amount") to determine the fate of the radionuclide using a scintillation camera prior to administering a therapeutic dose. Therapeutic doses will be administered in sufficient amounts to alleviate pain and/or inhibit tumor growth and/or cause regression of tumors and/or kill the tumor. Amounts of radionuclide needed to provide the desired therapeutic dose will be determined experimentally and optimized for each particular composition. The amount of radioactivity required to deliver a therapeutic dose will vary with the individual composition employed. For example, less activity will be needed for radionuclides with longer half lifes. The energy of the emissions will also be a factor in determining the amount of activity necessary. The composition to be administered may be given in a single treatment or fractionated into several portions and administered at different times. Administering the composition in fractionated doses may make it possible to minimize damage to non-target tissue. Such multiple dose administration may be more effective.

The compositions of the present invention may be used in conjunction with other active agents and/or ingredients that enhance the therapeutic effectiveness of the compositions and/or facilitate easier administration of the compositions.

Studies to determine the qualitative biodistribution of the various radionuclides were conducted by injecting the compositions into rats and obtaining the gamma ray images of the entire animal at various times up to two hours after injection.

Quantitative biodistributions were obtained by injecting 50–100 microliters of the composition into the tail vein of unanesthetized male Sprague Dawley rats. The rats were then placed in cages lined with absorbent paper in order to collect all urine excreted prior to sacrifice. After a given period of time, the rats were sacrificed by cervical dislocation and the various tissues dissected. The samples were then rinsed with saline, blotted dry on absorbent paper and weighed. The radioactivity in the samples was measured with a NaI scintillation counter.

The following examples are included to aid in the understanding of the invention but are not to be construed as limiting the invention.

EXAMPLE 1

In a 100-mL three necked round-bottomed flask equipped with a thermometer, reflux condenser, and heating mantle was added 3.48 g (20.2 mmole) of 1,4,7,10-tetraazacyclododecane and 14 ml of water. This solution was treated with 17.2 mL of concentrated HCl and 7.2 g of $H_3PO_3$ (87.8 mmole) and heated to 105° C. The refluxing suspension was stirrred vigorously and treated dropwise with 13 g (160.2 mmole) of formaldehyde (37 wt % in water) over a one hour period. At the end of this time the reaction was heated at reflux an additional 2 hours after which the heat was removed and the reaction solution allowed to cool and set at room temperature for 62.5 hours. The reaction solution was then concentrated in vacuo at 40° C. to a viscous reddish brown semisolid. A 30 mL portion of water was added to the semisolid which started to dissolve but then began to solidify. The whole suspension was then poured into 400 mL of acetone with vigorously stirring. The resulting off-white precipitate was vacuum filtered and dried overnight to give 10.69 g (97% yield) of crude DOTMP. A 2.0 g (3.65 mmole)

sample of the crude DOTMP was dissolved in 2 mL of water by the addition of 700 μL of concentrated ammonium hydroxide (10.0 mmole) in 100 μL portions to give a solution at pH of 2–3. This solution was then added all at once to 4.5 mL of 3N HCl (13.5 mmole), mixed well, and allowed to set. Within one hour small squarish crystals had begun to form on the sides of the glass below the surface of the liquid. The crystal growth was allowed to continue undisturbed for an additional 111 hours after which time the crystals were gently bumped off of the vessel walls, filtered, washed with 3 mL portions of water, four times, and air dried to constant weight to give 1.19 g (60% yield) of white crystalline solid DOTMP.

EXAMPLE 1A

A 250 mL three-necked, round-bottomed flask was loaded with 6.96 g (0.04 moles) of 1,4,7,10-tetraazacyclododecane. To this flask was added 14.5 g (0.177 moles) of phosphorous acid, 30 mL of deionized water and 28 mL of concentrated hydrochloric acid (0.336 moles).

The flask was attached to a reflux condenser and fitted with a stirbar, and a thermometer adapted with a thermowatch controller. A separate solution of 26.0 g (0.32 moles) of aqueous 37% formaldehyde solution was added to a 100 mL addition funnel and attached to the flask. The flask was brought to reflux temperature (about 105° C.) with vigorous stirring. The formaldehyde solution was added dropwise over a 30–40 minute interval. The solution was heated and stirred for an additional three hours then cooled slowly to ambient temperature.

The reaction solution was transferred to a 500 mL round-bottomed flask and attached to a rotary evaporation apparatus. The solution was taken down to a viscous, amber semi-solid (note-temperature never exceeded 40° C.). This semi-solid was treated with approximately 300 mL of HPLC grade acetone producing a light brown, sticky viscous oil. This oil was dissolved in 22 mL of water and added slowly with vigorous stirring to 1L of acetone. The acetone was decanted and the light colored oil dried under vacuum to give 16.6 g (76% yield) of crude DOTMP. To 13.1 g of this crude DOTMP was added 39.3 g of deionized water along with a seed crystal and the solution allowed to stand overnight. The resulting precipitate was vacuum filtered, washed with cold water, and dried under vacuum to give 4.75 g of DOTMP (36% yield).

A further purification was performed by dissolving 3.0 g (5.47 mmole) of DOTMP from above in 3 mL of water by the addition of 2.2 mL (31.5 mmole) of concentrated ammonium hydroxide. This solution was made acidic by the addition of 2.4 mL (28.8 mmole) of concentrated HCl at which time a white solid precipitated. This precipitate was vacuum filtered and dried to give 2.42 g (81% yield) of purified DOTMP characterized by a singlet at 11.5 ppm (relative to 85% $H_3PO_4$) in the $^{31}P$ decoupled NMR spectrum.

EXAMPLE 2

Sm-153 can be produced in a reactor such as the University of Missouri Research Reactor. Sm-153 is produced by irradiating 99.06 percent enriched $^{152}Sm_2O_3$ in the first row reflector at a neutron flux of $8 \times 10^{13}$ neutron/$cm^2$.sec. Irradiations were generally carried out for 50 to 60 hours, yielding a Sm-153 specific activity of 1000–1300 Ci/g.

To irradiate $Sm_2O_3$ for production of Sm-153, the desired amount of target is first weighed into a quartz vial, the vial flame sealed under vacuum and welded into an aluminum can. The can is irradiated for the desired length of time, cooled for several hours and opened remotely in a hot cell. The quartz vial is removed and transferred to a glove box, opened into a glass vial which is then sealed. An appropriate amount of a solution of hydrochloric acid is then added to the vial via syringe in order to dissolve the $Sm_2O_3$. Once the $Sm_2O_3$ is dissolved, the Samarium solution is diluted to the appropriate volume by addition of water. The solution is removed from the original dissolution vial which contains the chards of the quartz irradiation vial, and transferred via syringe to a clean glass serum vial.

EXAMPLE 3

Holmium-166 is prepared by weighing 0.5–1.0 mg of $Ho_2O_3$ into a quartz vial. The vial is sealed and placed in an aluminum can which is welded shut. The sample is irradiated (usually for about 24–72 hours) in the reactor (first row reflector, neutron flux of $8 \times 10^{13}$ neutron/$cm^2$.sec). After irradiation, the vial is opened and the oxide is dissolved using 4 N HCl. Heating may be necessary. Water is then used to dilute the sample to an appropriate volume.

EXAMPLE 4

Gadolinium-159 is prepared by sealing gadolinium oxide (1.1 mg) in a quartz vial. The vial is welded inside an aluminum can and irradiated for 30 hours in a reactor at a neutron flux of $8 \times 10^{13}$ neutron/$cm^2$.sec. The contents of the quartz vial is dissolved using HCl. Water is added to obtain a solution of Gd-159 in 0.1 N HCl.

When the procedure of Examples 2, 3 or 4 are repeated using the appropriate oxide, the radioisotopes of Ytterbium-175 (Yb-175) and Lutetium-177 (Lu-177) are prepared.

EXAMPLE 5

The ligand of Example 1 (22 mg) was dissolved in 878 μl of distilled water and 15 μl of 50% NaOH. A volume of 15 μl of this solution was transferred to a vial containing 1.5 mL of Sm solution (0.3 mM Sm in 0.1N HCl spiked with 2 μl of Sm-153 tracer). The pH was adjusted to 7–8 using NaOH and the amount of Sm found as a complex was >99% as determined by ion exchange chromatography. This yielded a solution containing Sm at 0.3 mM with a ligand to metal molar ratio of approximately 1.5.

Sprague Dawley rats were allowed to acclimate for five days then injected with 100 μL of the Sm solution described above via a tail vein. The rats weighed between 150 and 200 g at the time of injection. After 2 hours the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ. The percent of the injected dose in several tissues are given in Table I. The numbers represent the average of 3 rats per data point.

TABLE I

| INJECTED DOSE IN SEVERAL TISSUES FOR Sm-DOTMP[1] | |
|---|---|
| Bone | 58.1 |

TABLE I-continued

INJECTED DOSE IN SEVERAL TISSUES FOR Sm-DOTMP[1]

| Liver | 0.06 |
|---|---|
| Kidney | 0.27 |
| Spleen | 0.004 |
| Muscle | 0.15 |
| Blood | 0.004 |

[1]Ligand to Sm Molar Ratio of approximately 1.5

EXAMPLE 6

The ligand of Example 1 (22 mg) was dissolved in 878 µL of distilled water and 15 µL of 50% NaOH. A volume of 30 µL of this solution was transferred to a vial containing 1.5 mL of Ho solution (0.6 mM Ho in 0.1N HCl spiked with 2 µL of Ho-166 tracer). The pH was adjusted to 7-8 using NaOH and the amount of Ho found as a complex was greater than 99% as determined by ion exchange chromatography. This yielded a solution containing 0.6 mM Ho with a ligand to metal molar ratio of approximately 1.5.

Sprague Dawley rats were allowed to acclimate for five days then injected with 100 µL of the Ho solution described above via a tail vein. The rats weighed between 150 and 200 g at the time of injection. After 2 hours the rats were killed by cervical dislocation and dissected. The amount of radioactivity in each tissue was determined by counting in a NaI scintillation counter coupled to a multichannel analyzer. The counts were compared to the counts in 100 µL standards in order to determine the percentage of the dose in each tissue or organ. The percent of the injected dose in several tissues are given in Table II. The numbers represent the average of 3 rats per data point.

TABLE II

% INJECTED DOSE IN SEVERAL TISSUES FOR Ho-DOTMP[1]

| Bone | 57 |
|---|---|
| Liver | 0.07 |
| Kidney | 0.4 |
| Spleen | 0.006 |
| Muscle | 0.3 |
| Blood | 0.07 |

[1]Ligand to Ho Molar Ratio of approximately 1.5

EXAMPLE 7

A quantity of 14.5 mg of the ligand of Example 1A was placed in a vial and dissolved in 760 µL of water and 5 µL of 50% NaOH. A volume of 1100 µL of Sm solution (0.3 mM Sm in 0.1 N HCl) which was spiked with Sm-153, was placed in a separate vial and 10 µL of the ligand solution was added. The pH of the solution was adjusted to 7-8 using NaOH and the solution was passed through 3 plastic columns containing 1.5 mL of cation exchange resin (Sephadex™ C-25 from Pharmacia). The amount of Sm as a complex was determined to be 99% by cation exchange chromatography.

A volume of 1100 µL of Ho solution (0.6 mM Ho in 0.1 N HCl) which was spiked with Ho-166, was placed 30 in a separate vial and 20 µL of the above ligand solution was added. The pH of the solution was adjusted to 7-8 using NaOH and the solution was passed through 2 plastic columns containing 1.5 mL of cation exchange resin (Sephadex C-25 from Pharmacia). The amount of Ho as a complex was determined to be 99% by cation exchange chromatography.

Sprague Dawley rats were allowed to acclimate for five days then injected with 100 µL of the solutions described above via a tail vein. The rats weighted between 150 and 200 g at the time of injection. After 2 hours the rats were killed by cervical dislocation. Tissues were taken, weighed and the amount of radioactivity determined by counting in a NaI scintillation counter coupled to a multichannel analyzer. The counts in each tissue were compared to the counts in 100 µL standards in order to determine the percentage of the dose in each tissue or organ. The percent of the injected dose in several tissues are given in Table III. The numbers represent the average of 3 rats per data point.

TABLE III

% INJECTED DOSE IN SEVERAL TISSUES FOR DOTMP METAL COMPLEXES

|  | Sm | Ho |
|---|---|---|
| Bone | 50 | 64 |
| Liver | 0.37 | 0.19 |
| Kidney | 0.29 | 0.32 |
| Spleen | 0.04 | 0.05 |
| Muscle | 0.49 | 0.22 |
| Blood | 0.12 | 0.17 |

EXAMPLE 8

The ligand of Example 1A (14.5 mg) was placed in a vial and dissolved in 760 µL of water and 5 µL of 50% NaOH. A volume of 1000 µL of Gd solution (0.3 mM Gd in 0.1 N HCl) which contained tracer quantities of Gd-159, was placed in a separate vial and 15 µL of the ligand solution was added. The pH of the solution was adjusted to 7-8 using NaOH and the amount of Gd as a complex was determined to be >99% by cation exchange chromatography.

A Sprague Dawley rat was allowed to acclimate for five days then injected with 175 µL of the solution described above via a tail vein. The rat weighed 155 g at the time of injection. After 2 hours the rat was killed by cervical dislocation and dissected. The amount of radioactivity in each tissue was determined by counting in a NaI scintillation counter coupled to a multichannel analyzer. The counts in each tissue were compared to the counts in 175 µL standards in order to determine the percentage of the dose in each tissue or organ. The % of the injected dose in several tissues are given in Table IV.

TABLE IV

% INJECTED DOSE IN SEVERAL TISSUES FOR Gd-DOTMP[1]

| Tissue | % Dose |
|---|---|
| Bone | 50 |
| Liver | 0.08 |
| Kidney | 0.25 |
| Spleen | None Detected* |
| Muscle | 0.08 |
| Blood | 0.06 |

[1]Ligand to Gd molar ratio of approximately 1.5
*counts in the spleen were below background

EXAMPLE 9

The ligand of Example 1A (15.8 mg) was dissolved in 963 µL of distilled water and 8 µL of 50% NaOH. A volume of 15 µL of this solution was transferred to a vial containing 1.5 mL of Lu solution (0.3 mM Lu in 0.1N HCl spiked with 2 µL of Lu-177 tracer). The pH was adjusted to 7-8 using NaOH and the amount of Lu found as a complex was greater than 99% by ion exchange chromatography. This yielded a solution containing 0.3 mM Lu with a ligand to metal molar ratio of approximately 1.5.

Sprague Dawley rats were allowed to acclimate for five days then injected with 100 μL of the Lu solutions described above via a tail vein. The rats weighed between 150 and 200 g at the time of injection. After 2 hours the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ. The percent of the injected dose in several tissues are given in Table V. The numbers represent the average of 3 rats per data point.

TABLE V

| % INJECTED DOSE IN SEVERAL TISSUES FOR Lu-DOTMP[1] | |
|---|---|
| Tissue | % Dose |
| Bone | 54 |
| Liver | 0.08 |
| Kidney | 0.3 |
| Spleen | 0.006 |
| Muscle | 0.04 |
| Blood | 0.09 |

[1]Ligand to Lu molar ratio of approximately 1.5.

EXAMPLE A (COMPARATIVE)

In a method similar to that previously used, compositions were prepared containing complexes of Sm-153 with several commercially available phosphonic acids which do not contain the alkylene linkage between the nitrogen and the phosphorus atoms.

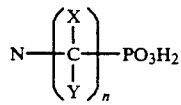

The two hour biolocalization of Sm-153 in rats for these compositions was determined as previously described. The results are given in Table VI. The ligands used include methylendiphosphonic acid (MDP) and hydroxyethylidinediphosphonic acid (HEDP) which contain a $P\text{-}CH_2\text{-}PO_3H_2$ and a $P\text{-}C(CH_3)(OH)\text{-}PO_3H_2$ linkage, respectively: pyrophosphate (PYP) which contains a $P\text{-}O\text{-}PO_3H_2$ linkage: and imidodiphosphate (IDP) which contains a $N\text{-}PO_3H_2$ linkage. Metal complexes of these ligands are known skeletal agents. For example, Tc complexes of MDP, HEDP, and PYP have been used commercially as diagnostic bone agents. However, these ligands were inadequate for selectively delivering Sm-153 to the skeletal system as exemplified by the large fraction of the radioactivity found in the liver and/or blood.

Table VI shows the biolocalization of Sm-153 in rats two hours after injection and the results represent the percent of injected dose in tissue.

TABLE VI

| % Dose In | Sm-153 MDP | Sm-153 HEDP | Sm-153 PYP | Sm-153 IDP |
|---|---|---|---|---|
| Bone | 2 | 21 | 2 | 0.6 |
| Liver | 85 | 3.5 | 73 | 36 |
| Blood | 0.23 | 13 | 0.23 | 0.04 |

The numbers given in Table VI for Sm-153-MDP, Sm-153-HEDP, Sm-153-PYP and Sm-153-IDP represent the average of the results of five, five, three and three rats, respectively.

We claim:

1. A composition suitable for administration to an animal having bone pain or having one or more calcific tumors comprising a complex which comprises a macrocyclic aminophosphonic acid or a physiologically acceptable salt thereof containing 1,4,7,10-tetraazacyclododecane as the macrocyclic moiety and wherein the nitrogen and phosphorous are interconnected by an alkylene or substituted alkylene radical of the formula

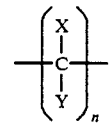

wherein X and Y are independently selected from the group consisting of hydrogen, hydroxyl, carboxyl, phosphonic, and hydrocarbon radicals having from 1–8 carbon atoms and physiologically acceptable salts of the acid radicals, and n is 1–3 with the proviso that when n > 1, each X and Y may be the same as or different from the X and Y of any other carbon atom, and at least one radionuclide selected from the group consisting of Sm-153, Gd-159, Ho-166, Lu-177, and Yb-175 and wherein the resulting composition is therapeutically effective for the relief of bone pain or treatment of calcific tumors.

2. The composition of claim 1 wherein the radionuclide is Gd-159.

3. The composition of claim 1 wherein the radionuclide is Sm-153.

4. The composition of claim 1 wherein the radionuclide is Lu-177.

5. The composition of claim 1 wherein the radionuclide is Yb-175.

6. The composition of claim 1 wherein the radionuclide is Ho-166.

7. The composition of claim 1 wherein X and Y are hydrogen and n is 1.

8. The composition of claim 1 wherein the ligand to radionuclide molar ratio is at least about 1:1.

9. The composition of claim 1 wherein the macrocyclic aminophosphonic acid has the structure

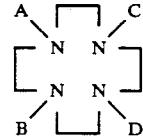

wherein substituents A, B, C, and D are independently ted from hydrogen, hydrocarbon radicals having from 1–8 carbon atoms,

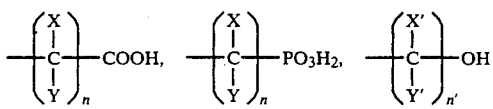

and physiologically acceptable salts of the acid radicals wherein X, Y, and n are as previously defined, X' and Y' are independently hydrogen, methyl, or ethyl radicals, n' is 2 or 3, with the proviso that at least two of said nitrogen substituents is a phosphoruscontaining group.

10. The composition of claim 9 wherein the radionuclide is Gd-159.

11. The composition of claim 9 wherein the radionuclide is Sm-153.

12. The composition of claim 9 wherein the radionuclide is Lu-177.

13. The composition of claim 9 wherein the radionuclide is Yb-175.

14. The composition of claim 9 wherein the radionuclide is Ho-166.

15. The composition of claim 9 wherein the macrocyclic aminophosphonic acid is 1,4,7,10-tetraazacyclododecanetetramethylenephosphonic acid or a physiologically acceptable salt.

16. The composition of claim 15 wherein the radionuclide is Gd-159.

17. The composition of claim 15 wherein the radionuclide is Sm-153.

18. The composition of claim 15 wherein the radionuclide is Yb-175.

19. The composition of claim 15 wherein the radionuclide is Lu-177.

20. The composition of claim 15 wherein the radionuclide is Ho-166.

21. The composition of claim 15 wherein the ligand to radionuclide molar ratio is about 1:1 to about 3:1.

22. The composition of claim 15 wherein the ligand to radionuclide molar ratio is about 1:1 to about 1.5:1.

23. A sterile composition suitable for administration to an animal having bone pain or having one or more calcific tumors comprising at least one radionuclide selected from the group consisting of Samarium-153, Gadolinium-159, Holmium-166, Ytterbium-175, and Lutetium-177 complexed with at least one macrocyclic aminophosphonic acid or a physiologically acceptable salt thereof, containing the 1,4,7,10-tetraazacyclododecane moiety wherein the nitrogen and phosphorus are interconnected by an alkylene or substituted alkylene radical of the formula

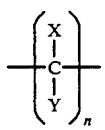

wherein X and Y are independently selected from the group consisting of hydrogen, hydroxyl, carboxyl, phosphonic, and hydrocarbon a radicals having from 1-8 carbon atoms and physiologically acceptable salts of the acid radicals, and n is 1-3 with the proviso that when n>1, each X and Y may be the same as or different from the X and Y of any other carbon atom; and wherein the radionuclide in dosage form is present in an amount containing at least 0.02 mCi per kilogram of body weight of said animal.

24. The composition of claim 23 wherein the ligand to radionuclide molar ratio is at least about 1:1.

25. The composition of claim 23 wherein the macrocyclic aminophosphonic acid is 1,4,7,10-tetraazacyclododecanetetramethylenephosphonic acid or a physiologically acceptable salt thereof.

26. The composition of claim 23 wherein the radionuclide is Sm-153.

27. The composition of claim 23 wherein the radionuclide is Ho-166.

28. The composition of claim 23 wherein the radionuclide is Gd-159.

29. The composition of claim 23 wherein the radionuclide is Yb-175.

30. The composition of claim 23 wherein the raionuclide is Lu-177.

31. The composition of claim 25 wherein the ligand to radionuclide molar ratio is about 1:1 to about 3:1.

32. The composition of claim 25 wherein the ligand to radionuclide molar ratio is about 1:1 to about 1.5:1.

33. A pharmaceutical formulation comprising the composition of claim 1 and a pharmaceutically acceptable carrier.

34. The formulation of claim 33 wherein the radionuclide is Gd-159.

35. The formulation of claim 33 wherein the radionuclide is Sm-153.

36. The formulation of claim 33 wherein the radionuclide is Lu-177.

37. The formulation of claim 33 wherein the radionuclide is Yb-175.

38. The formulation of claim 33 wherein the radionuclide is Ho-166.

39. A pharmaceutical formulation comprising the composition of claim 9 and a pharmaceutically acceptable carrier.

40. The formulation of claim 39 wherein the radionuclide is Gd-159.

41. The formulation of claim 39 wherein the radionuclide is Sm-153.

42. The formulation of claim 39 wherein the radionuclide is Lu-177.

43. The formulation of claim 39 wherein the radionuclide is Yb-175.

44. The formulation of claim 39 wherein the radionuclide is Ho-166.

45. A pharmaceutical formulation comprising the composition of claim 15 and a pharmaceutically acceptable carrier.

46. The formulation of claim 45 wherein the radionuclide is Gd-159.

47. The formulation of claim 45 wherein the radionuclide is Sm-153.

48. The formulation of claim 45 wherein the radionuclide is Lu-177.

49. The formulation of claim 45 wherein the radionuclide is Yb-175.

50. The formulation of claim 45 wherein the radionuclide is Ho-166.

51. A pharmaceutical formulation comprising the composition of claim 23 and a pharmaceutically acceptable carrier.

52. The formulation of claim 51 wherein the radionuclide is Gd-159.

53. The formulation of claim 51 wherein the radionuclide is Sm-153.

54. The formulation of claim 51 wherein the radionuclide is Lu-177.

55. The formulation of claim 51 wherein the radionuclide is Yb-175.

56. The formulation of claim 51 wherein the radionuclide is Ho-166.

57. A method for the therapeutic treatment of an animal having one or more calcific tumors which comprises administering to said animal a therapeutically effective amount of at least one composition comprising a complex which comprises at least one macrocyclic aminophosphonic acid or a physiologically acceptable salt thereof containing 1,4,7,10-tetraazacyclododecane as the macrocyclic moiety and wherein the nitrogen and phosphorous are interconnected by an alkylene or substituted alkylene radical of the formula

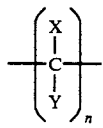

wherein X and Y are independently selected from the group consisting of hydrogen, hydroxyl, carboxyl, phosphonic, and hydrocarbon radicals having from 1–8 carbon atoms and physiologically acceptable salts of the acid radicals, and n is 1–3 with the proviso that when n>1, each X and Y may be the same as or different from the X and Y of any other carbon atom, and at least one radionuclide selected from the group consisting of Sm-153, Gd-159, Ho-166, Lu-177 and Yb-175.

58. The method of claim 57 wherein the radionuclide is Gd-159.

59. The method of claim 57 wherein the radionuclide is Sm-153.

60. The method of claim 57 wherein the radionuclide is Lu-177.

61. The method of claim 57 wherein the radionuclide is Yb-175.

62. The method of claim 57 wherein the radionuclide is Ho-166.

63. The method of claim 57 wherein X and Y are hydrogen and n is 1.

64. The method of claim 57 wherein the macrocyclic aminophosphonic acid has the structure

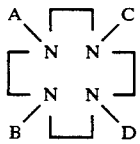

wherein substituents A, B, C, and D are independently selected from hydrogen, hydrocarbon radicals having from 1–8 carbon atoms,

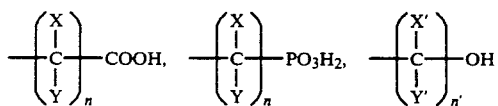

and physiologically acceptable salts of the acid radicals wherein X, Y, and n are as previously defined, X' and Y' are independently hydrogen, methyl, or ethyl radicals, n' is 2 or 3, with the proviso that at least two of said nitrogen substituents is a phosphorus containing group.

65. The method of claim 64 wherein the radionuclide is Gd-159.

66. The method of claim 64 wherein the radionuclide is Sm-153.

67. The method of claim 64 wherein the radionuclide is Lu-177.

68. The method of claim 64 wherein the radionuclide is Ho-166.

69. The method of claim 64 wherein the radionuclide is Yb-175.

70. The method of claim 64 wherein the macrocyclic aminophosphonic acid is 1,4,7,10-tetraazacyclododecanetetramethylenephosphonic acid or a physiologically acceptable salt.

71. The method of claim 70 wherein the radionuclide is Gd-159.

72. The method of claim 70 wherein the radionuclide is Sm-153.

73. The method of claim 70 wherein the radionuclide is Yb-175.

74. The method of claim 70 wherein the radionuclide is Lu-177.

75. The method of claim 70 wherein the radionuclide is Ho-166.

76. The method of claim 70 wherein the animal is a human.

77. A method for the therapeutic treatment of an animal having bone pain which comprises administering to said animal a therapeutically effective amount of at least one composition comprising a complex which comprises at least one macrocyclic aminophosphonic acid or a physiologically acceptable salt thereof containing 1,4,7,10-tetraazacyclododecane as the macrocyclic moiety and wherein the nitrogen and phosphorous are interconnected by an alkylene or substituted alkylene radical of the formula

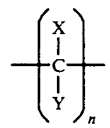

wherein X and Y are independently selected from the group consisiting of hydrogen, hydroxyl, carboxyl, phosphonic, and hydrocarbon radicals having from 1–8 carbon atoms and physiologically acceptable salts of the acid radicals, and n is 1–3 with the proviso that when n>1, each X and Y may be the same as or different from the X and Y of any other carbon atom, and at least one radionuclide selected from the group consisting of Sm-153, Gd-159, Ho-166, Lu-177, and Yb-175.

78. The method of claim 77 wherein the radionuclide is Gd-159.

79. The method of claim 77 wherein the radionuclide is Sm-153.

80. The method of claim 77 wherein the radionuclide is Lu-177.

81. The method of claim 77 wherein the radionuclide is Ho-166.

82. The method of claim 77 wherein the radionuclide is Yb-175.

83. The method of claim 77 wherein the macrocyclic aminophosphonic acid is 1,4,7,10-tetraazacyclododecanetetramethylenephosphonic acid or a physiologically acceptable salt.

84. The method of claim 83 wherein the radionuclide is Gd-159.

85. The method of claim 83 wherein the radionuclide is Sm-153.

86. The method of claim 83 wherein the radionuclide is Yb-175.

87. The method of claim 83 wherein the radionuclide is Lu-177.

88. The method of claim 83 wherein the radionuclide is Ho-166.

* * * * *

UNITED STATES PATENT AND TRADEMARK OFFICE
CERTIFICATE OF CORRECTION

PATENT NO. : 5,059,412

DATED : October 22, 1991

INVENTOR(S) : Jaime Simon et al

It is certified that error appears in the above-indentified patent and that said Letters Patent is hereby corrected as shown below:

Under other publications, line 8, "1964" should correctly appear as -- 1984 --.

Column 14, line 67, "ted" should correctly appear as -- selected --.

Column 15, line 12, "phosphoruscontaining" should correctly appear as -- phosphorus-containing --.

Column 16, line 9, "claim 23" should correctly appear as -- claim 25 --; line 11, "claim 23" should correctly appear as -- claim 23 --; line 13, "claim 23" should correctly appear as -- claim 25 --; line 15, "claim 23" should correctly appear as -- claim 25 --; line 17, "claim 23" should correctly appear as -- claim 25 --.

Signed and Sealed this

Third Day of August, 1993

Attest:

MICHAEL K. KIRK

Attesting Officer

Acting Commissioner of Patents and Trademarks